United States Patent [19]

Tominaga et al.

[11] Patent Number: 4,710,561

[45] Date of Patent: Dec. 1, 1987

[54] [POLY]IMIDAZOLINE ADDUCT FOR ELECTROCOATING

[75] Inventors: Akira Tominaga; Reiziro Nishida, both of Hiratsuka, Japan

[73] Assignee: Kansai Paint Co., Ltd., Hyogo, Japan

[21] Appl. No.: 935,306

[22] Filed: Nov. 26, 1986

[30] Foreign Application Priority Data

Nov. 27, 1985 [JP] Japan .................. 60-265101

[51] Int. Cl.$^4$ ........................... C08G 59/64
[52] U.S. Cl. ........................ 528/111; 528/96; 528/117; 528/407; 528/361; 528/369; 525/504; 523/415; 523/416; 428/413; 204/291
[58] Field of Search ............... 528/96, 111, 117, 407, 528/361, 369; 525/504; 523/415, 416; 428/413; 204/291

[56] References Cited

U.S. PATENT DOCUMENTS 3,896,082  7/1975  Rensmann ..................... 528/117

*Primary Examiner*—John Kight
*Assistant Examiner*—Frederick Krass
*Attorney, Agent, or Firm*—Wenderoth, Lind & Ponack

[57] ABSTRACT

A resin coating composition comprising an epoxy resin derivative having an imidazoline ring functional group of the formula

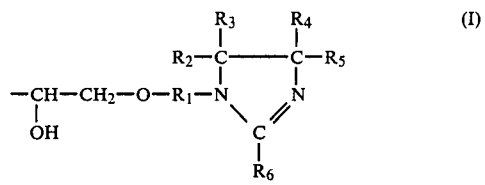

wherein $R_1$ represents an alkylene group having 2 to 6 carbon atoms, each of $R_2$, $R_3$, $R_4$ and $R_5$ represents a hydrogen atom or a methyl group, and $R_6$ represents a residue of a carboxylic acid, as a resin binder. This resin coating composition is useful for cationic electrodeposition coating.

20 Claims, No Drawings

[POLY]IMIDAZOLINE ADDUCT FOR ELECTROCOATING

This invention relates to a new resin coating composition. More specifically, the invention relates to a resin coating compsotion having improved corrosion resistance to make it especially suitable for cationic electrodeposition coating.

In the past, polyamine resins such as amine-added epoxy resins have been used as resin binders in cationic electrodeposition coating compositions. For example, there have been used as the resin binders an adduct between a polyepoxide and a primary mono- or polyamine, a secondary polyamine or a primary and a secondary polyamine (see, for example, U.S. Pat. No. 3,984,299); an adduct between a polyepoxide and a secondary mono- or polyamine having a ketiminized primary amino group (see, for example, U.S. Pat. No. 4,017,438); and a reaction product obtained by the etherification of a polyepoxide and a hydroxy compound having a ketiminized primary amino group (see, for example, Japanese Laid-Open Patent Publication No. 43,013/1984). These polyamine resins are cured with an alcohol-blocked isocyanate compound to form an electrodeposited film. Although such an electrodeposited film is given a fair rating of corrosion resistance, it is still unsatisfactory where a high degree of corrosion resistance is desired as in the present-day automobile finishing. It is strongly desired therefore to improve these polyamine resins used for electrodeposition.

The present inventors previously proposed an epoxy resin derivate obtained by introducing an oxazolidine ring functional group via an ether linkage into the epoxy groups of an epoxy resin as a component of a resin binder in a resin coating composition which far surpasses a resinous coating composition comprising the aforesaid amine-added epoxy resin as a resin binder in corrosion resistance and has good other film properties and electrodeposition properties (Japanese Patent Application No. 197780/1985 corresponding to U.S. patent application Ser. No. 905327 and European Patent Application No. 86112414.7).

This epoxy resin derivative, however, does not have entirely satsifactory dispersibility in water when neutralized with a small amount of a neutralizing agent. For example, the neutralization equivalent may be about 50 equivalent %, but it should have a neutralization value of at least 15 (mg of KOH/g of resin solids). When it is used as a binder for cationic electrodeposition coating compositions, it suffers from some defects, among which are:

(a) the coulomb efficiency is low;
(b) it is difficult to obtain a smooth coated film having a large thickness; and
(c) its stability in an emulsion region is low.

In view of these defects, the present inventors furthered their studies, and have now found that a resin coating composition having excellent corrosion resistance as a coated film and good dispersibiltiy in water at a low neutralization value can be obtained by using as a component of a resin binder an epoxy resin derivative obtained by introducing an imidazolidine ring functional group into the epoxy groups of an epoxy groups of an epoxy resin by etherification.

Thus, according to this invention, there is provided a resin coating composition comprising an epoxy resin derivative having an imidazoline ring functional group represented by the following formula.

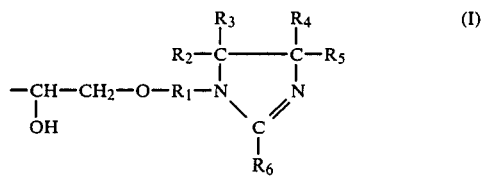

wherein $R_1$ represents an alkylene group having 2 to 6 carbon atoms, each of $R_2$, $R_3$, $R_4$ and $R_5$ represents a hydrogen atom or a methyl group, and $R_6$ represents a residue of a carboxylic acid, as a resin binder.

The epoxy resin derivative having an imidazoline ring functional group used as a resin binder in the resin coating composition of this invention is obtained by introducing an imidazoline group into an epoxy resin as a base resin. Introduction of the imidazoline ring can be carried out, for example, by reacting an N-hydroxyalkylimidazoline with the 1,2-epoxy groups of an epoxy resin.

The N-hydroxyalkylimidazoline (iii) used in the production of the epoxy resin derivative can be obtained, for example, by reaction between an N-(beta-aminoalkyl)alkanolamine (i) and a carboxylic acid (ii) in accordance with the following scheme.

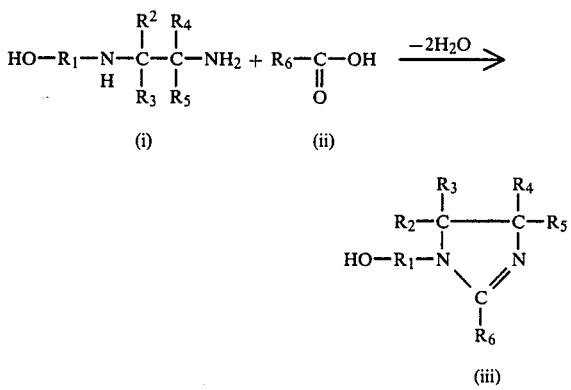

In the above formulae, $R_1$ represents an alkylene group having 2 to 6 carbon atoms, particularly $-CH_2CH_2-$ or

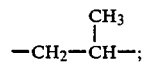

each of $R_2$, $R_3$, $R_4$ and $R_5$ represents a hydrogen atom or methyl group; and $R_6$ represents a residue of a carboxylic acid; for example a hydrogen atom or a saturated or unsaturated aliphatic hydrocarbon group having 1 to 36 carbon atoms, preferably 1 to 18 carbon atoms, which may contain a hydroxyl group or an ether linkage, particularly a hydrogen atom or a $C_1$-$C_2$ alkyl or alkenyl group which may be substituted by the hydroxyl group.

Examples of the N-(beta-aminoalkyl)alkanolamine (i) used in the above reaction are a 1:1 adduct or ethylenediamine and a monoepoxide, N-(beta-aminoethyl)ethanolamine, N-(beta-aminoethyl)isopropanolamine, N-(beta-aminopropyl)ethanolamine, and N-(beta-aminopropyl)isopropanolamine. N-(beta-aminoethyl)e- thanolamine [the compound of formula (i) in which $R_1$ is $C_2H_4$, and $R_2$, $R_3$, $R_4$ and $R_5$ are H] is most suitable because of its low price and high reactivity.

Examples of the carboxylic acid (ii) include aliphatic monocarboxylic acids having 1 to 18 carbon atoms such as formic acid, acetic acid, propionic acid, 2-ethylhexanoic acid, palmitic acid and linoleic acid, hydroxy fatty acids having 1 to 18 carbon atoms such as hydroxyacetic acid, lactic acid and ricinoleic acid, and dicarboxylic acids having 1 to 36 carbon atoms such as maleic acid, adipic acid, sebacic acid and dimeric acid (dimerized linoleic acid). Where the dicarboxylic acids are used, the above reaction usually gives bis-N-hydroxyalkylimidazolines of the following formula.

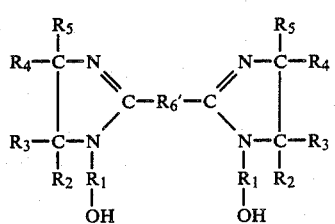
(iii-1)

In this case, $R_6$ represents an aliphatic hydrocarbon group (which may further contain an ether linkage) substituted by a group of the formula (iv) below.

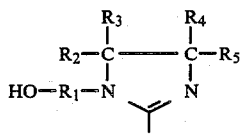
(iv)

It should be understood that for the purpose of the present invention, the aliphatic hydrocarbon group $R_6'$ in which $R_6'$ is a residue of a dicarboxylic acid, such as a $C_1$–$C_{36}$ alkylene group or a $C_2$–$C_{36}$ alkenylene group (which may be interrupted by an ether linkage) is included within the definition of the carboxylic acid residue $R_6$.

Of these carboxylic acids, acetic acid, formic acid ($R_6$=H), hydroxyacetic acid ($R_6$=$CH_2OH$), propionic acid ($R_6$=$C_2H_5$) and lactic acid ($R_6$=$C_2H_4OH$) are preferred.

The reaction of the N-(beta-aminoalkyl)alkanolamine (i) with the carboxylic acid (ii) is carried out by using the carboxylic acid (ii) in a stoichiometrically equivalent amount with respect to the N-(beta-aminoalkyl)alkanolamine (i), heating them at a temperature of 100° to 240° C., preferably 140° to 200° C., and removing the resulting water. To remove the resulting water as an azeotrope, an inert solvent such as toluene or xylene is preferably added.

Next, the resulting N-hydroxyalkyloxazolidine (iii) is reacted with the 1,2-epoxy groups of an epoxy resin to give an imidazoline ring functional group-containing epoxy resin derivative, the resin binder used in this invention. This reaction proceeds as schematically shown below.

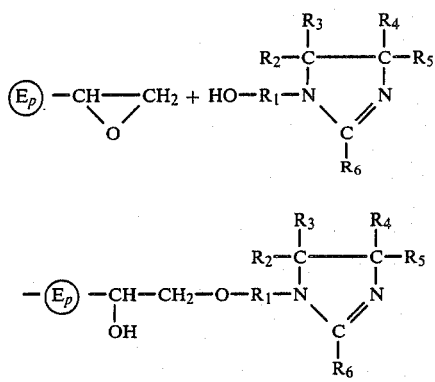

In the above scheme $E_p$ represents the skeleton portion of the epoxy resin. Although in the above scheme only one epoxy group is shown for simplicity, it is to be understood that in addition, at least one other epoxy group is bonded. $R_1$, $R_2$, $R_3$, $R_5$ and $R_6$ have the same as defined hereinbefore.

An especially preferred imidazoline ring functional group of formula (I) introduced into the epoxy resin base in this manner is represented by the formula

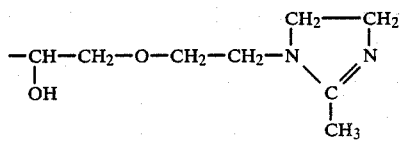

Polyepoxide compounds containing at least about two 1,2-epoxy groups

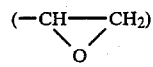

on an average per molecule and having a number average molecular weight of at least 200, preferably from 400 to 4000, and more preferably from 800 to 2000 are suitably used as the epoxy resin in the forefoing reaction. They may be chosen from polyepoxide compounds known per se. For example, they include polyglycidyl ethers of polyphenols that can be produced by reacting polyphenols with epichlorohydrin in the presence of an alkali. Typical examples of such polyepoxide compounds are glycidyl ethers of polyphenols such as bis(4-hydroxphenyl)-2,2-propane, bis(4-hydroxyphenyl)1,1-ethane, bis(4-hydroxphenyl)methane, 4,4'-dihydroxydiphenyl ether, 4,4'-dihydroxydiphenylsulfone, phenol novolak and cresol novolak, and polymers thereof.

From the standpoint of cost and corrosion resistance, the polyglycidyl ethers of polyphenols having a number average molecular weight of at least about 380, preferably about 800 to 200, and an epoxy equivalent ranging from 190 to 2000, preferably 400 to 1000, are preferred. Especially preferred is a polyepoxide compound having the following general formula

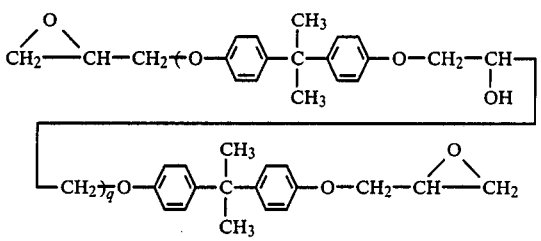

wherein q is from 0 to 4.

On the other hand, when properties other than corrosion resistance are important, there can also be used alicyclic polyglycidyl ethers such as bis(4-hydroxycyclohexyl)-2,2-propane and bis(4-hydroxycyclohexyl)methane; polyglycidyl esters of polycarboxylic acids such as terephthalic acid and tetrahydrophthalic acid; epoxidized 1,2-polybutadiene; and glydicyl (meth)acrylate copolymers.

The reaction between the epoxy resin and the N-hydroxyalkylimidazoline proceeds by just heating the reactants usually at 80° to 140° C., preferably 100° to 120° C., in the absence or presence of a solvent such as alcohols, ketones or ethers. When a mono-N-hydroxyalkylimidazoline is used as the N-hydroxyalkylimidazoline, the equivalent ratio of the 1,2-epoxy groups of the epoxy resin to the N-hydroxyalkylimidazoline is not necessarily critical, but for avoiding gellation by the remaining epoxy groups, the equivalent ratio of 1,2-epoxy groups to the N-hydroxyalkyloxazolidine should usually be in the range of from 2/1 to 1/1, preferably from 1.5/1 to 1/1. When the ratio exceeds the above-specified limit, it is desirable to react part of the 1,2-epoxy groups in advance with a reactant such as in amine, a phenol or a carboxylic acid. On the other hand, when a bis-N-hydroxyalkylimidazoline is used as the N-hydroxyalkylimidazoline, the N-hydroxyalkylimidazoline group may be stoichiometrically excessive with respect to the 1,2-epoxy groups. To avoid gellation, the equivalent ratio of the 1,2-epoxy groups to the N-hydroxyalkylimidazoline groups is preferably from 1/1 to 1/2, especially from 1/1.2 to 1/1.8.

The amount (number) of the imidazoline groups to be introduced is usually 0.1 to 2.2 groups, and preferably 0.2 to 1.0 group, per 1000 gram of the resin solids. If this amount is less than 0.1 group, the dispersibility of the resin in water is insufficient. Amounts exceeding 2.0 groups cause the defect that the amount of an acid required for solubilizing the resin becomes too great. The resulting epoxy resin derivative may have an amine value of usually 10 to 140, preferably 20 to 70.

The term "amine value", as used herein, is the amount of KOH equivalent to HCl required for neutralizing one gram of the resin, and is shown in milligrams per gram of resin.

As required, another function may be imparted to the resulting epoxy resin derivative by reacting the remaining unreacted 1,2-epoxy groups with another reagent. For example, the following functions may be imparted.

(A) By reaction with another amine-type reagent having active hydrogen, the basicity and hydrophilicity of the epoxy resin derivative can be controlled. Examples of the amine reactants used for this purpose include ketimines formed from methyl isobutyl ketone and di-ethanolamine, ethyl ethanolamine or monoethanmine, oxazolidine from diethanolamine and formaldedhyde, hydrazine, and hydroxyethyl hydrazine.

(B) By reaction with monocarboxylic acids, monophenols or monoalcohol, the viscosity of the epoxy resin derivative may be lowered to improve the smoothness of the resulting coated film. Examples of the reactants used for this purpose are 2-ethylhexanoic acid, linoleic acid, nonylphenol and 2-ethylhexanol.

(C) The film properties of the epoxy resin derivative may be improved by reacting it with a hydroxy-, carboxy-, or amino-terminated polyester, polyether, polyurethane, polyamide or polybutadiene to modify it. Examples of the modifier used for this purpose include polycaprolactone diol, polypropylene glycol, polytetramethylene glycol, dimeric acid polyamide, and a carboxyterminated acrylonitrile/butadiene copolymer.

Preferably, the reaction of the epoxy resin derivative with the reagents or modifiers in (A), (B) and (C) above is carried out prior to the reaction of the epoxy groups with the N-hydroxyalkylimidazoline. At times, it may be carried out simultaneously with, or after, this reaction.

The amount of the reagent or modifier used in modifying the epoxy resin derivative is not particularly critical if it is within a range which does not impair the properties of the epoxy resin itself. Generally, the weight ratio of the reagent or modifier to the epoxy resin is not more that ½, preferably not more than ¼.

To impart heat-curability to the imidazoline group-containing epoxy resin derivative, a crosslinking functional group may be introduced into the epoxy resin deprivative, or an external curing agent may be used together. Examples of the crosslinking functional group are a blocked isocyanate group, a beta-hydroxy ester group, an alpha,beta-unsaturated carbonyl group and an N-methylol group which are all known. Active carbamic acid ester groups of the formula

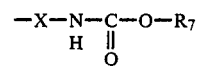

wherein X is a tertiary nitrogen atom, an oxygen atom or a sulfur atom, or an aliphatic hydrocarbon group having 1 to 6 carbon atoms containing the above atoms at both ends, and $R_7$ a hydroxyl- or alkoxy-containing aliphatic hydrocarbon group having 1 to 12 carbon atoms which may contain an ether linkage, are especially convenient to use in view of their low temperature curability.

Examples of the carbamic acid esters are shown below.

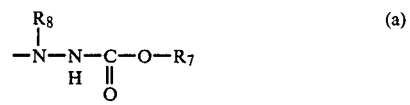

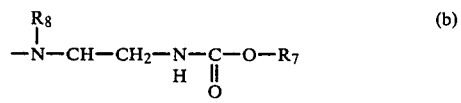

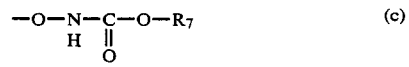

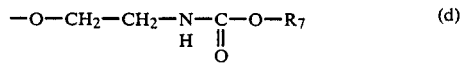

-continued

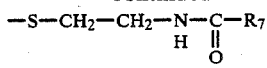

In the above formulae, $R_7$ is as defined above, and $R_8$ is a methyl, ethyl, hydroxyethyl, aminoethyl or or ethyl alkylcarbamate group.

When corrosion resistance is considered, the group (a) obtained from hydrazine and an alkylene carbonate is most preferred.

The active carbamate functional groups described hereinabove are known per se. They are fully disclosed in, for example, U.S. Pat. No. 4,528,363, and reference may therefore be made to this U.S. patent for a detailed description of the active carbamate functional groups.

Compounds having at least two of the aforesaid crosslinking groups per molecule may be used as the external curing agent. Examples of such compounds are blocked polyisocyanates, beta-hydroxyethyl esters of polycarboxylic acids, malonic esters, methylolated melamine and methylolated urea. Most preferred as the external curing agents are compounds having the above-described active carbamate groups, for example a compound obtained by reacting 1 mole of a diglycidyl either of bisphenol A with an adduct of 2 moles of diethylene triamine and 4 moles of ethylene carbonate.

The imidazoline functional group-containing epoxy resin derivative may be rendered water-dispersible by protonating the imidazoline group with a water-soluble organic carboxylic acid such as formic acid, acetic acid and lactic acid. The amount of the acid to be used in protonation cannot be strictly defined. But generally, it is preferred in view of electrodeposition properties to neutralize the epoxy resin derivative until the neutralization value becomes about 5 to 40 mg of KOH, especially about 10 to 20 mg of KOH, per gram of the resin solids. The imidazoline group is hydrolyzed more or less in the aqueous dispersion to reproduce the secondary amino group as shown by the following scheme.

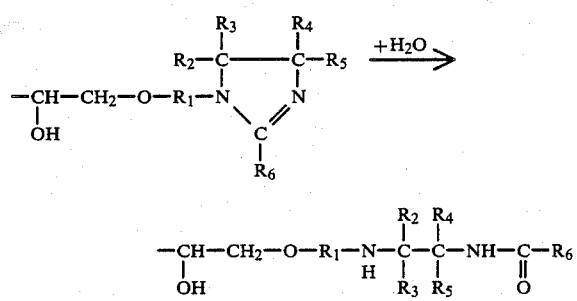

Accordingly, the stability, heat-curability and corrosion resistance of the aqueous dispersion of the epoxy resin derivative are further improved.

This aqueous dispersion is especially suitable for use in cationic electrodeposition coating. If required, the aqueous is used for electrode-position after adding pigments, solvents, curing catalysts, surfactants, etc.

In carrying out the electrodeposition coating of an article with this aqueous dispersion, known methods and apparatuses that have been used heretofore in cationic electrodeposition coating can be used without modification. In the electrodeposition coating operation, the article to be coated is used as the cathode, and a stainless steel or carbon plate is preferably used as the anode. There are no particular restrictions imposed on the conditions used to carry out the electrodeposition coating. Generally, the electrodeposition coating is desirably carried out with agitation at a bath temperature of 20° to 30° C., a voltage of 100 to 400 V, preferably 200 to 300 volts and a current density of 0.01 to 3 A/dm² while adjusting the current passing time to 1 to 5 minutes, the electrode area ratio (A/C) to 2/1 to ½, and the interelectrode distance to 10 to 100 cm.

The coated film electrodeposited on the article (the cathode) can, after washing, be cured by baking at about 150° to 180° C.

The composition of this invention, in addition to its use as a resin binder in the above-described cationic electrodeposition coating, can also be used as a binder for a solvent-type paint binder by dilut it with an ordinary solvent.

The following examples illustrate the present invention more specifically. All parts and percentages in these examples are by weight.

EXAMPLE 1

Sixty parts (1 mole) of acetic acid was added little by little to 104 parts (1 mole) of N-(beta-aminoethyl) ethanolamine and 16 parts of toluene. After generation of the heat of neutralization reaction ceased, the mixture was heated under reflux at 150° to 160° C. until 36 parts (2 moles) of water distilled. Finally, the solvent was removed under reduced pressure to give 128 parts of N-hydroxyethyl-2-methylimidazoline (amine value about 440). Then, 380 parts (1 mole) of bisphenol A diglycidyl ether having an epoxy equivalent of about 190, 85 parts (0.1mole) of polycaprolactone diol having a hydroxyl equivalent of about 425 and 1.28 parts of the N-hydroxyethyl-2-methylimidazoline obtained above were mixed under heat, and reacted at 140° C. until the epoxy value of the product decreased to 3.8 (mg equivalent/1 g of solids; the same unit applies hereinafter), and then 114 parts (0.5 mole) of bisphenol A was added, and the mixture was reacted at 130° C. until the epoxy value of the product decreased to 1.35. Then, the reaction mixture was diluted with 219 parts of ethylene glycol monobutyl ether and cooled. An 80% aqueous solution of a diethylene-triamine/ ethylene carbonate adduct (mole ratio 1:2) prepared in advance (139.5 parts; 0.4 mole) was added, and the misture was reacted at 90° C. until the amine value of the product decreased to 2 or below (mg of KOH/g of resin solids; the same unit applies hereinafter). The reaction mixture was further reacted with 38.4 parts (0.3 mole) of the above N-hydroxyethyl -2-methylimidazoline until there was no rise in viscosity. As a result, an epoxy resin derivative in accordance with this invention was obtained.

The resulting epoxy resin derivative (133.8 parts; resin solids 100 parts), 1 part of polypropylene glycol (Sannix PP-4000, a tradename for a product of Sanyo Chemical Co., Ltd.) and 1.07 part acetic acid (neutralization value 10 mg of KOH) were mixed, and deionized water was gradually added to disperse the epoxy resin derivative in water to give an emulsoion having a resin solids content of 15%, a pH of 6.0 and an average particle diameter of 0.1 micron. The emulsion had good stability.

Five parts of 20% lead acetate was added to the resulting emulsion to prepare an electrodeposition bath. A zinc phosphate-treated steel panel (Bt#3080 made by Nihon Parkerizing Co., Ltd.) was coated by electrodeposition from the bath at 250 V while the temperature of the bath was maintained at 28° C., and then subjected to baking at 160° C. for 20 minutes to give a smooth coated film having a thickness of about 35 microns. The coated film had good salt spray resistance (2000 hours).

EXAMPLE 2

475 Parts (0.5 mole) of bisphenol A-type epoxy resin having an epoxy equivalent of 475 (Epikote 1001, a tradename for a product of Yuka-Shell Co., Ltd.) was dissolved under heat in 235 parts of ethylene glycol monobutyl ether, and 47.5 parts (0.5 mole) of an 80% aqueous solution of hydroxyethylhydrazine was added. The mixture was reacted at 70° C. until the amine value of the product decreased to not more than 1. Ethylene carbonate (44 parts; 0.5 mole) was added, and the mixture was reacted at 90° C. until the amine value of the product no longer decreased. Then, 219 parts (0.5 mole) of dimeric acid/bis-N-hydroxyethylimidazoline reaction product having an amine value of 154 (Hartall M-34, a tradename for a product of Harima Chemical Co., Ltd.) was added to the reaction mixture, and the mixture was reacted at 95° C. until there was no rise in viscosity. As a result, an epoxy resin derivative in accordance with the invention was obtained.

The epoxy resin derivative (118 parts; resin solids 90 parts), 10 parts of methy ethyl ketone oxime blocked isophorone diisocyanate and 1 part of polypropylene glycol (PP-4000) were mixed, and 1.28 parts (neutralization value 12) of acetic acid was added. The mixture was heated to about 60° C., and with stirring, deionized water was gradually added to disperse the epoxy resin derivative in water to give an emulsion having a resin solids content of 30%, an average particle diameter of 0.2 micron and a pH of 5.8. The emulsion had good stability.

Three parts of basic lead silicate, 13 parts of titanium white, 0.3 parts of carbon black, 3 parts of clay, 2 parts of dibutyltin oxide and 1 part of a nonionic surfactant (Noigen 142B, a tradename for a product of Daiichi Kogyo Seiyaku Co., Ltd.) were added to the resulting emulsion, and the mixture was ball-milled to a particle size of less than 10 microns. The resulting dispersion was diluted with deionized water to a resin solids content of 15% to prepare an electrodeposition coating bath. A phosphate-treated steel panet (Bt#3080) was coated by electrodeposition from the electrodepostion coating bath at 220 V while the temperature of the bath was maintained at 30° C., and then subjected to baking at 150° C. for 20 minutes to give a smooth coated film having a thickness of about 30 microns. The coated film had good salt spray resistance (1500 hours).

EXAMPLE 3

650 Parts (0.5 mole) of bisphenol A-type epoxy resin having an epoxy equivalent of 650 (Epikote 1002, a tradename for a product of Yuka-Shell Co., Ltd.) was dissolved in 246 parts of ethylene glycol monobutyl ether, and 85.8 parts (0.6 mole) of monoethanolamine/methyl isobutyl ketone ketimine was added. The mixture was reacted until the amine value of the product decreased to 1 or below. Then, 105 parts (0.3 mole) of tall oil fatty acid/N-hydroxyethylimidazoline reaction product having an amine value of 160 (Hatall M-33, a tradename for a product of Harima Chemical Co., Ltd.) was added, and the mixture was reacted at 100° C. until there was no rise in viscosity. As a result, an epoxy resin derivative in accordance with this invention was obtained.

The resulting epoxy resin derivative (104 parts; resin solids 80 parts), 20 parts of ethylene glycol mono-2-ethylhexyl ether blocked 4,4'-diphenylmethane diisocyanate and 1 part of polypropylene glycol (PP-4000) were mixed, and 1.28 parts (neutralization value 12) of acetic acid was added. The mixture was heated to 60° C., and with stirring, deionized water was gradually added to disperse the epoxy resin derivative in water to give an emulsion having a resin solids content of 30%, an average particle diameter of 0.15 micron and a pH of 6.3. The emulsion had good stability.

Using the resulting emulsion, an electrode-position coating bath was prepared in the same way as in Example 2. A phosphate-treated steel panel (Bt#3080) was coated by electrodepositon from the electrodeposition coating bath at 280 V, and then subjected to baking at 170° C. for 20 minutes to give a smooth coated film having a thickness of about 25 microns. The coated film had good salt spray resistance (2000 hours).

What we claim is:

1. A resin coating composition comprising an epoxy resin derivative having an imidazoline ring functional group of the formula

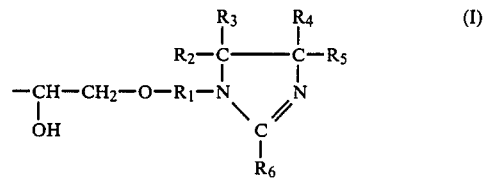

wherein $R_1$ represents an alkylene group having 2 to 6 carbon atoms, each of $R_2$, $R_3$, $R_4$ and $R_5$ represents a hydrogen atom or a methyl group, and $R_6$ represents a residue of a carboxylic acid,
as a rest binder.

2. A resin coating composition of claim 1 wherein the group of formula (I) is an imidazoline ring functional group obtained by reacting the 1,2-epxoy groups of an epoxy resin with an N-hydroxyimidazoline of the formula

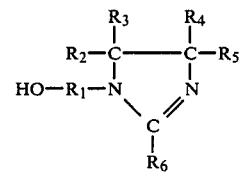

wherein $R_1$, $R_2$, $R_3$, $R_4$, $R_5$ and $R_6$ are as defined in claim 1.

3. A resin coating composition of claim 1 wherein $R_1$ is the group —$CH_2CH_2$—.

4. A resin coating composition of claim 1 wherein each of $R_2$, $R_3$, $R_4$ and $R_5$ is a hydrogen atom.

5. A resin coating composition of claim 1 wherein $R_6$ represents a hydrogen atom or a saturated or unsaturated aliphatic hydrocarbon group having 1 to 36 carbon atoms which may contain a hydroxyl group or an ether linkage.

6. A resin coating composition of claim 1 wherein $R_6$ represents $CH_3$, $CH_2OH$, $C_2H_5$ or $C_2H_4OH$.

7. A resin coating composition of claim 1 wherein the imidazoline ring functional group has the formula $$-\underset{\underset{OH}{|}}{CH}-CH_2-O-CH_2-CH_2-N\underset{\underset{CH_3}{|}}{\overset{CH_2-CH_2}{\diagup}}N$$

8. A resin coating composition of claim 2 wherein said epxoy resin is a polyepoxide compound containing at least about two 1,2-epoxy groups on an average per molecule and having a number average molecular weight of at least 200.

9. A resin coating composition of claim 8 wherein said polyepoxide compound is a polyglycidyl ether of a polyphenol having a number average molecular weight of at least about 380 and an epoxy equivalent ranging from 190 to 2000.

10. A resin coating composition of claim 9 wherein said polyepoxide compound is a glycidyl ether of a polyphenol selected from the group consisting of bis(4-hydroxyphenyl)-2,2-propane, bis(4-hydroxyphenyl)-1,1-ethane, bis(4-hydroxyphenyl)-methane, 4,4'-dihydroxydiphenyl ether, 4,4'-dihydroxydiphenylsulfone, phenol novolak and cresol novolak.

11. A resin coating composition of claim 9 wherein said polyepoxide compound has the formula

[structure of diglycidyl ether of bisphenol A oligomer, with subscript q]

wherein q is a number from 0 to 4.

12. A resin coating composition of claim 1 wherein said epoxy resin derivative has 0.1 to 2.0 imidazoline ring functional groups per 1000 grams of said resin derivative.

13. A resin coating composition of claim 1 wherein said epoxy resin derivative has an active carbamic acid ester functional group in addition to the group of formula (I).

14. A resin coating composition of claim 13 wherein said active carbamic acid ester functional group has the formula $$-X-\underset{H}{N}-\underset{\underset{O}{\|}}{C}-O-R_7$$

wherein X is a tertiary nitrogen atom, an oxygen atom or a sulfur atom, or an aliphatic hydrocarbon group having 1 to 6 carbon atoms which contains said atoms at both ends; and $R_7$ is a hydroxyl group or an aliphatic hydrocarbon group having 1 to 12 carbon atoms which may contain an ether linkage.

15. A resin coating composition of claim 14 wherein said active carbamic acid ester functional group has the formula $$-\underset{\underset{H}{|}}{N}-\underset{R_8}{\overset{|}{N}}-\underset{\underset{O}{\|}}{C}-O-R_7$$

wherein $R_8$ is a methyl, ethyl, hydroxyethyl, aminoethyl or ethyl alkylcarbamate group; and $R_7$ is as defined in claim 14.

16. A resin coating composition of claim 1 further containing an external curing agent.

17. A resin coating composition of claim 1 wherein said imidazoline ring functional group has been protonized with a water-soluble organic carboxylic acid.

18. A cationic electrodeposition coating bath formed of the resin coating composition of claim 1.

19. The use of the resin coating composition of claim 1 in cationic electrodeposition coating.

20. An article coated with the resin coating composition of claim 1.

* * * * *